United States Patent
Yiu

Patent Number: 6,159,222
Date of Patent: Dec. 12, 2000

[54] DEVICE FOR HAIR REMOVAL

[75] Inventor: Wai-Wah Yiu, Kowloon, The Hong Kong Special Administrative Region of the People's Republic of China

[73] Assignee: Soft Lines Ltd., Kowloon, The Hong Kong Special Administrative Region of the People's Republic of China

[21] Appl. No.: 09/270,617

[22] Filed: Mar. 17, 1999

Related U.S. Application Data

[60] Provisional application No. 60/078,239, Mar. 17, 1998.

[51] Int. Cl.$^7$ .................................................. A61B 17/41
[52] U.S. Cl. ............................................ 606/133; 606/131
[58] Field of Search ............................ 606/36, 43, 131, 606/133

[56] References Cited

U.S. PATENT DOCUMENTS

| | | |
|---|---|---|
| 853,096 | 5/1907 | Lewis . |
| 1,071,978 | 9/1913 | White . |
| 1,743,590 | 1/1930 | Binz ........................................ 606/133 |
| 2,417,530 | 3/1947 | Weiser . |
| 2,486,616 | 11/1949 | Schubiger .............................. 606/133 |
| 2,888,927 | 6/1959 | Fozard . |
| 2,894,512 | 7/1959 | Tapper . |
| 3,054,405 | 9/1962 | Tapper . |
| 3,088,470 | 5/1963 | Hall . |
| 4,174,713 | 11/1979 | Mehl . |
| 4,274,413 | 6/1981 | Hahn et al. . |
| 4,923,460 | 5/1990 | Amit ........................................ 606/133 |
| 4,935,024 | 6/1990 | Dolev ..................................... 606/133 |
| 5,057,116 | 10/1991 | Zucker . |
| 5,100,413 | 3/1992 | Dolev ..................................... 606/133 |
| 5,100,414 | 3/1992 | Dolev . |
| 5,163,288 | 11/1992 | Doley . |
| 5,226,907 | 7/1993 | Tankovich . |
| 5,230,303 | 7/1993 | Rubino . |
| 5,281,233 | 1/1994 | Doley . |
| 5,419,344 | 5/1995 | DeWitt . |
| 5,425,728 | 6/1995 | Tankovich . |
| 5,595,568 | 1/1997 | Anderson et al. . |
| 5,630,811 | 5/1997 | Miller . |
| 5,827,294 | 10/1998 | Mehl, Sr. ............................... 606/133 |
| 5,846,252 | 12/1998 | Mehl, Sr. ............................... 606/133 |

FOREIGN PATENT DOCUMENTS

| | | | |
|---|---|---|---|
| 1198964 | 9/1916 | Germany ............................. 606/131 |
| 299319 | 9/1916 | Germany ............................. 606/133 |
| 203970 | of 1916 | United Kingdom .................. 606/133 |

*Primary Examiner*—Paul J. Hirsch
*Assistant Examiner*—Michael B. Priddy

[57] ABSTRACT

The invention relates to a depilatory device having a compressible coil spring positioned between two arms which may be used to grasp and pluck hair for temporary hair removal or to radiate radio waves to permanently destroy hairs that are either proximal to the coil spring or held between the coils of the coil spring.

9 Claims, 4 Drawing Sheets

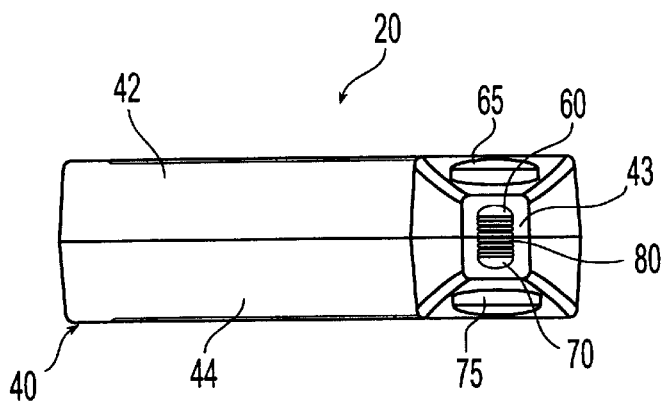
Fig. 2c
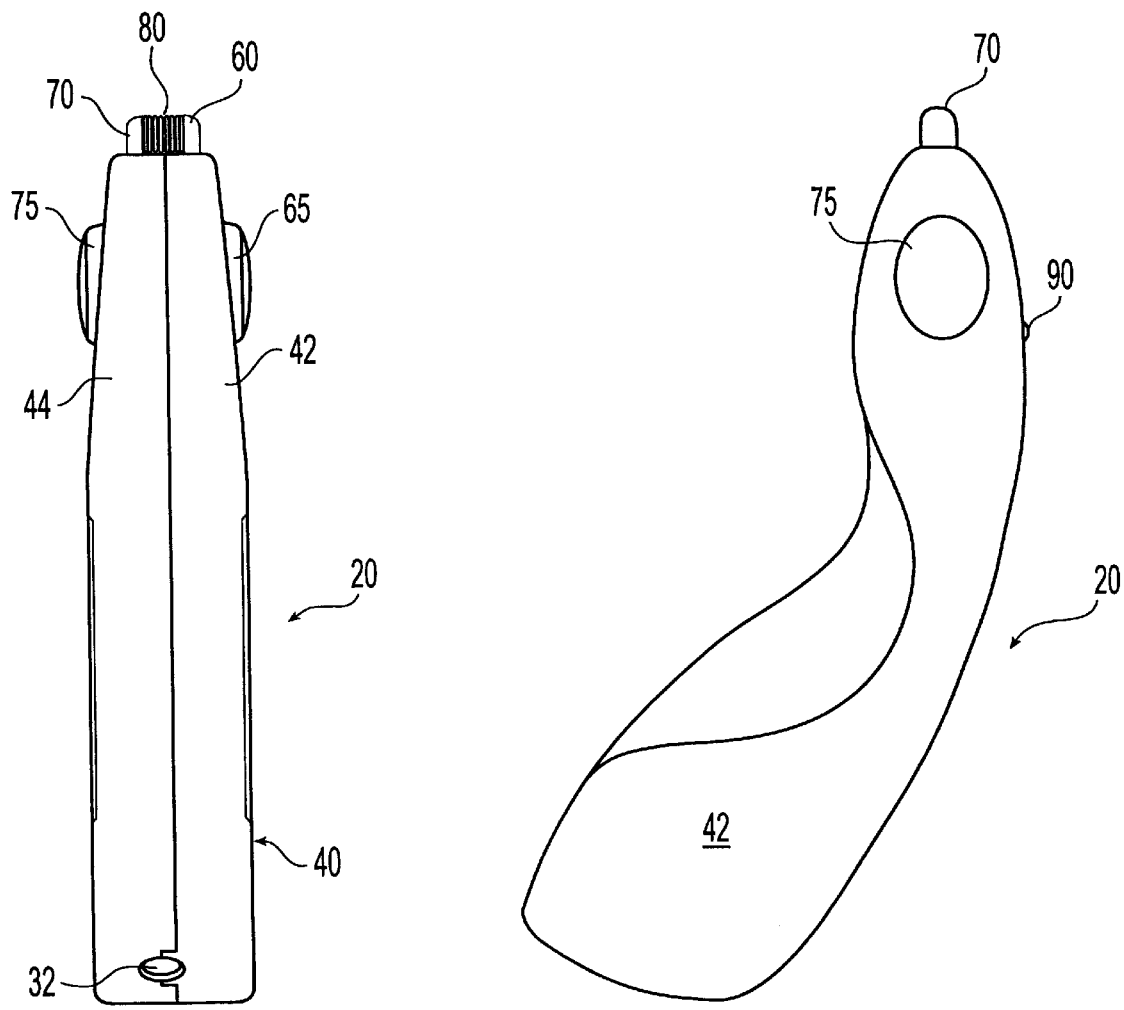
Fig. 2b
Fig. 2a

DEVICE FOR HAIR REMOVAL

This application claims priority to U.S. Provisional Application No. 60/078,239 filed Mar. 17, 1998, which is incorporated herein by reference in its entirety.

FIELD OF THE INVENTION

The present invention relates generally to a device for removal of unwanted hair either temporarily or permanently.

BACKGROUND OF THE INVENTION

There exists a need for the removal of unwanted hair to maintain desired personal appearance. There are many different devices known in the art that are useful for removing unwanted hair, such as razors, tweezers, and depilatory devices.

Although razors provide quick and easy hair removal, hair remains visible at the surface of the skin and quickly regrows. Therefore one must shave frequently in order to maintain smooth skin and a desired appearance. Tweezers also may be used. Prior art tweezers comprise two arms that are resiliently biased away from each other, each arm having an opposing surface. The hair is positioned between the two opposing surfaces, and the arms are pressed together, thereby grasping the hair between the two opposing surfaces of the tweezer arms. The hair is then plucked from the body. Tweezers provide longer-lasting hair removal. However, removing hair with tweezers is a tedious process since traditional tweezers can only remove one hair at a time. In addition, precise handling is required in order to position and grasp the hair between the two, usually small, opposing surfaces. In addition, because the hair is forcibly pulled from the skin, this is a painful process.

Alternatively, permanent depilatory devices may be used. These devices use high frequency electricity to destroy hair-producing papilla at the base of the hair shaft. However, many of these devices involve large and expensive equipment, and therefore require a visit to a salon and an appointment with a skilled operator. However, salon visits can be expensive and inconvenient since many people do not have the time to make regular visits. In addition, salon visits do not provide the privacy many people would like. Therefore, there is a need for a simple, convenient device that may be operated safely, effectively, and privately.

One of the well-known techniques for hair removal involves high frequency coagulation of the root of the hair. According to this technique, a needle is inserted into a follicle adjacent to the unwanted hair in order to reach the matrix area which contains the hair-producing papilla. High frequency electrical waves are then applied by the needle to the matrix area or papilla, thereby destroying it. Frequently, these devices include a tweezer used to pull the hair out of the follicle once the matrix area or papilla has been destroyed. These types of devices are illustrated in U.S. Pat. No. 3,054,405 to Tapper, U.S. Pat. No. 2,894,512 to Tapper, and U.S. Pat. No. 853,096 to Lewis. There are several drawbacks to these devices. Even with a skilled operator, patients may be cut or burned by the needle. The insertion of the needle under the skin is invasive and painful, particularly in tender skin areas, and may produce irritation, swelling, and burning of the skin tissues. In addition, only one hair can be treated and removed at a time. Accordingly, the removal of hair is a painful, uncomfortable, and tedious process, particularly where large areas of hair are to be removed.

More recently, there has been increasing use of a hair removal device using a tweezer with two arms that serve as electrodes. The tweezer arms are squeezed together to grip the hair at a considerable distance from the skin, and the electrode arms are charged with high frequency electrical current that flows along the hair shaft to its root.

The electrical current then coagulates the root, destroying the hair, which may then be removed. Such devices are shown in U.S. Pat. No. 2,888,927 to Fozard, U.S. Pat. No. 2,417,530 to Weiser, and U.S. Pat. No. 1,071,978 to White.

In addition, there are prior art devices which utilize radio frequency energy or current to coagulate the root of the hair. Specifically, U.S. Pat. No. 4,274,413 to Hahn discloses a depilatory tweezer, wherein the tweezer alms function as electrodes. To use this device, a hair is gripped precisely between the electrically conductive surfaces of the electrodes, and radio frequency is applied to the hair to bring about the coagulation of its root. In addition, U.S. Pat. No. 4,174,713 to Mehl discloses a hair removal device that applies concentrated radio frequency energy to a hair, thereby inducing conduction along the internal section of the hair shaft and downwardly to the matrix area to permanently damage the hair.

All of the devices described above require electric current to pass through the hair shaft in order to successfully effect hair destruction. However, there are problems with such devices. For example, in the tweezer electrode design described above, the electrodes may easily come into contact with each other when the tweezer arms are squeezed together (as with, for example, very fine hairs), thereby short circuiting the device, in which case electricity will not pass through the hair shaft. In order to ensure a complete circuit through the hair, the hair has to be grasped precisely between the tweezer electrodes. In addition, because hair is not a good conductor of electricity, the electrical energy has to be sufficiently high to induce conduction through the hair and destruction of the matrix area. In addition, the electrodes have to be held on the hair close to the skin to ensure that the high frequency energy reaches the matrix area. Unless the root is sufficiently coagulated, unwanted hair may reappear.

Such high frequency electrical energy must be kept away from the skin to prevent damage to the skin. Even in the hands of a skilled operator, there is danger of the electrode touching the skin, which will burn and sometimes scar the skin.

Since the above methods remove only one hair at a time, they are tedious and time consuming even when applied to small skin areas.

None of the depilatory devices discussed above provides for a device having a completed electric circuit before engaging the hair. The designs described above require the hair to complete the circuit. In one embodiment of the present invention, by contrast, radio waves are applied to the hair through a coil spring that is placed proximal to or in contact with the hair. This design overcomes the aforementioned difficulties of the prior art devices.

SUMMARY OF INVENTION

The invention relates to an improved tweezer mechanism comprising a compressible coil spring attached to a first and a second arm, wherein hair is grasped between the coils of the coil spring and subsequently pulled from the body. The coil spring may be used to grasp multiple hairs.

The invention also relates to a depilatory device comprising a compressible coil spring that is placed proximal to or used to grasp one or more hairs. The device also comprises a first arm and a second arm that are resiliently biased away from two ends of a compressible coil spring. A switch is activated when the first arm, the second arm, or both arms are pressed. Radio frequency energy is directed to proximal hair-producing papilla area(s), thereby destroying the papilla (s). The compressible coil spring can be used to grasp multiple hairs.

One feature of this invention is to provide a device which substantially reduces the time required to effectively remove hair.

Yet another feature of this invention is to provide a hair grasping assembly particularly constructed to focus radio waves at the contact area with the hair to substantially damage the matrix area.

A further feature of the invention is to provide a hair removal device which permits the application of radio waves simultaneously to several papilla areas.

A still further feature of this invention is its capability of applying radio waves to a hair in an amount and frequency sufficient to damage the papilla area.

Another feature of this invention is the provision of a readily operable device in which the hair is grasped and radio waves are applied substantially simultaneously.

A still further feature of the invention is the provision of a hand-held hair removal device in which the hair grasping elements may have alternative configurations.

An additional feature of this invention is the provision of apparatus which can easily be used to remove hair in difficult and inaccessible area, such as the nose, ear, face, breasts, and bikini line.

BRIEF DESCRIPTION OF THE DRAWINGS

Reference is next made to a brief description of the drawings, which are intended to illustrate the device according to the present invention. The drawings and detailed description which follow are intended to be merely illustrative, and are not intended to limit the scope of the invention as set forth in the appended claims.

FIG. 2A is a side view of the device of the present invention;

FIG. 2B is a front view of the device;

FIG. 2C is a top view of the device;

DETAILED DESCRIPTION OF THE INVENTION

Figure 1:
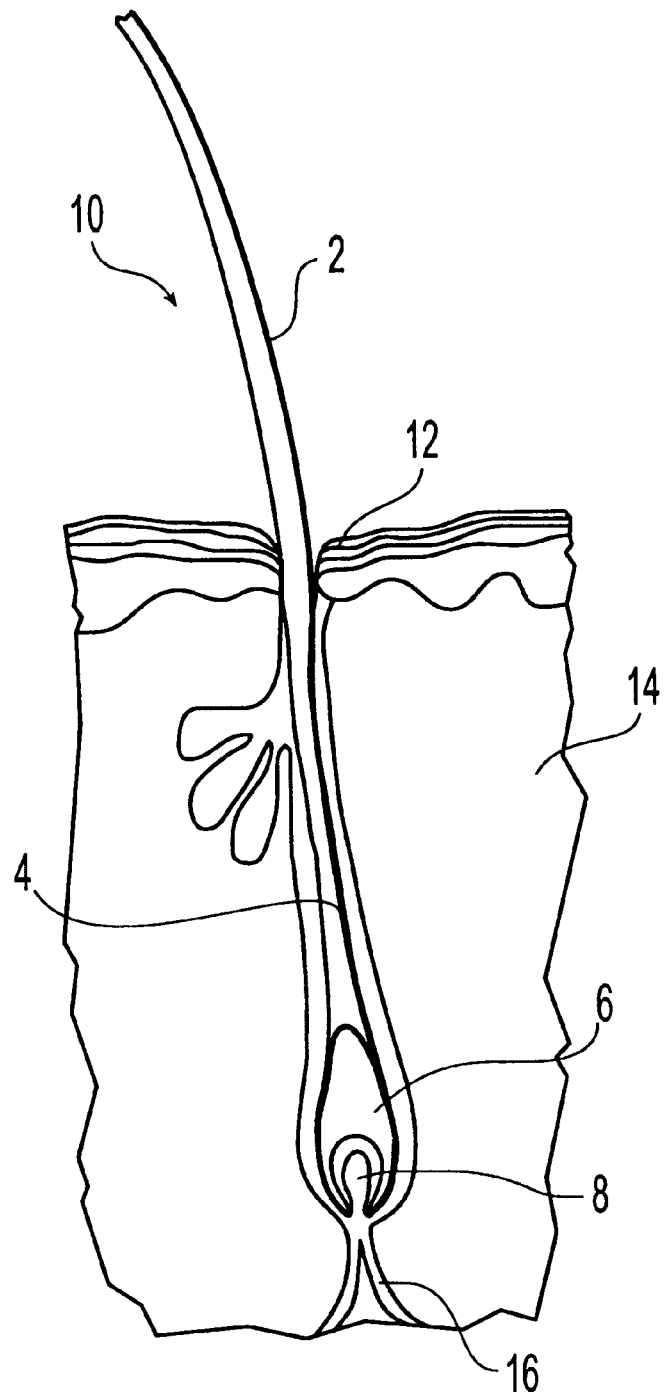
FIG. 1 is a cross-sectional view of a hair and surrounding skin tissue.

As shown in FIG. 1, hair 10 generally has an upper shaft portion 2 which extends above skin surface 12 and surrounding tissue 14, and a lower shaft portion 4 extending beneath the skin surface 12. Both upper and lower shaft portions 2, 4 are composed primarily of horny, fibrous cells that have coalesced. Matrix area 6 contains the growing area for hair 10. The growing area includes papilla 8, which is supplied with nutrients through blood vessel 16. To destroy hair permanently, matrix area 6 or papilla area 8 must be reached and destroyed. All other tissues of hair 10 comprise dead fibrous material; therefore, damage to this tissue (via other hair removal techniques such as shaving and tweezing) will not prevent future hair growth.

The target for the radio wave is the papilla 8, the matrix area 6, and the adjacent cellular structure immediately thereabove at the base of the lower shaft portion 4.

Figure 3A:
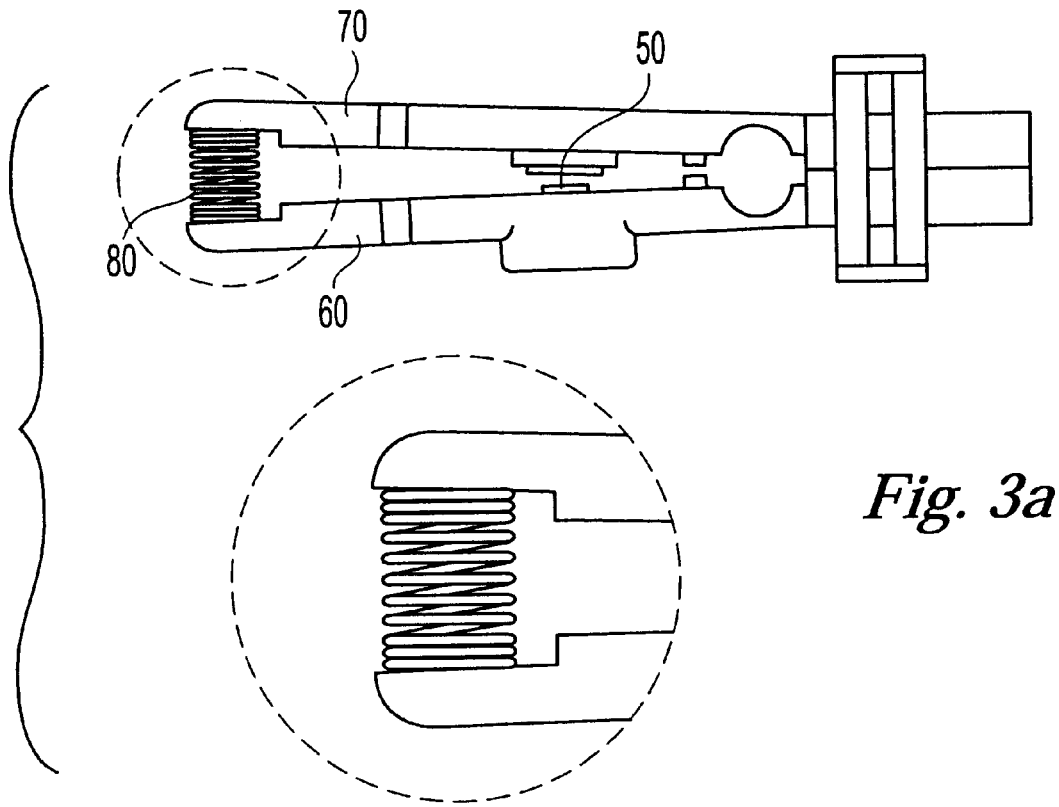
FIGS. 3A and 3B are side views of a portion of the device showing details of the arms.
Figure 3B:
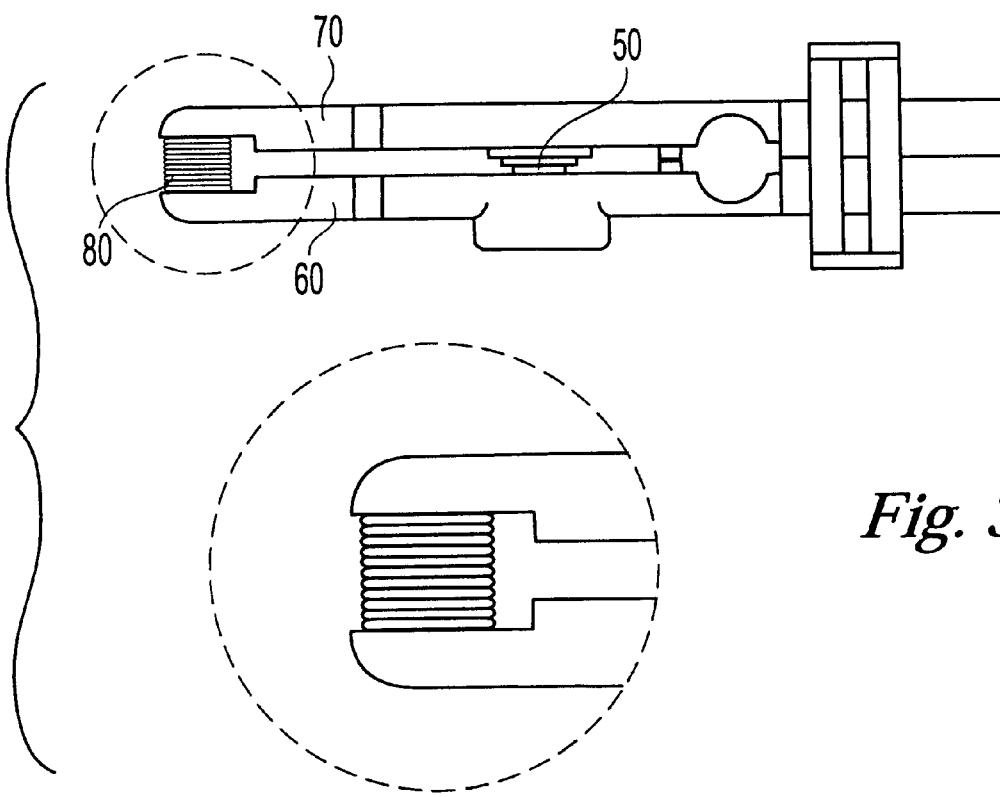
Figure 4:
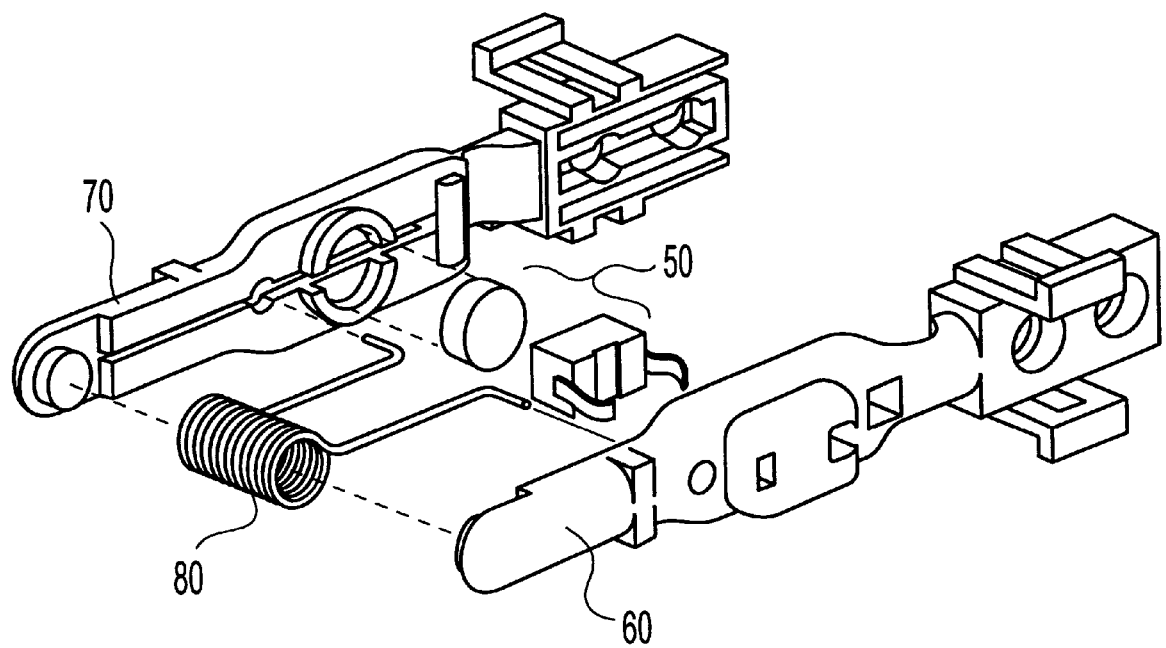
FIG. 4 is a disassembled view of the portions shown in FIGS. 3A and 3B.

The device of the present invention is generally shown in FIGS. 2A, 2B, and 2C, and portions of the device are shown in more detail in FIGS. 3A, 3B, and 4.

As shown in FIG. 2A, device 20 comprises outer casing 40, which houses electrical circuitry (not shown), first arm 60 connected to first button 65, second arm 70 connected to second button 75, and coil spring 80 having two ends connected to first arm 60 and second arm 70. In use, device 20 is plugged into a standard outlet via an AC-DC adapter having a cord, which is plugged into opening 32 in outer casing 40.

As shown in FIGS. 2A–C, device 20 is a lightweight hand-held device, which is ergonomically designed to fit comfortably in the palm of the hand. It is approximately 5.5 inches long and 1.0 to 1.5 inches wide. The components of the present invention are constructed of commercially available materials, the selection of which is within the ability of the ordinary skilled worker.

The electrical circuitry within outer casing 40 and coil spring 80, along with the AC-DC adapter and cord, provide the circuitry for the electrical energy that powers device 20. The arrangement and construction of these elements are known in the art. For example, the AC-DC adapter used with device 20 may be a standard off-the-shelf class 2 transformer, with an AC input of 120V, 60 Hz, and 6 W, and a DC output of 6V and 200 mA.

Outer casing 40 is made of an insulative material, such as plastic, nylon, or any other non-conductive material and may be attractively decorated with decals, trademark symbols, or other ornamental designs. Alternatively, brief instructions for use or warnings regarding improper use may be printed on the outer casing 40.

As shown in FIGS. 2A and 2C, outer casing 40 comprises upper section 42 and lower section 44. As shown in FIG. 2C, both upper and lower sections 42, 44 together form arm opening 43 through which first arm 60 and second arm 70 extend.

First arm 60 and second arm 70 are also made of an insulative material, such as plastic. Both arms 60, 70 are movably positioned within outer casing 40 and extend outside outer casing 40 through arm opening 43. As shown in FIGS. 3A, 3B, and 4, one end of coil spring 80 is attached to first arm 60, and the other end of coil spring 80 is attached to second arm 70. First arm 60 is also connected to first button 65, such that manually pressing first button 65 compresses coil spring 80 toward or against second arm 70. In addition, second arm 70 is connected to second button 75, such that manually pressing second button 75 compresses coil spring 80 toward or against first arm 60. First and second buttons 65, 75 may be pressed independently or simultaneously to squeeze one or both arms 60, 70 toward the other in a manner similar to tweezer arms. As shown in FIGS. 3A, 3B, and 4, when one or both arms 60, 70 are pressed, switch 50 is activated, which in turn activates the electrical circuitry of device 20.

In order to operate device 20, one or more hairs is placed or positioned within or proximal to the coils of coil spring 80. Then the user pushes first button 65, second button 75, or both buttons 65, 75, thereby compressing the coils of coil spring 80 and activating the electrical circuitry which generate radio waves. The radio waves have an effective frequency range known in the art and are generated via a signal generator. The output terminals of the signal generator are connected to the electrical circuitry of device 20.

When either or both buttons 65, 75 are pushed and the electrical circuitry of device 20 is activated, radio wave energy emanates to the hairs that are proximal to coil spring 80 and destroys the matrix area or papilla area. The user may then pull out the hair from its follicle, which should slide out easily. The user may use coil spring 80 to pull out the dead hair, or may alternatively use a pair of tweezers.

Optionally, device 20 may include indicator light 90 connected to the electric circuitry as shown in FIG. 2B such that it lights up when device 20 is plugged in. Additionally, indicator light 90 may have variable brightness, one to indicate that device 20 has been plugged in and one to indicate that switch 50 has been activated and coil spring 80 has been compressed.

Device 20 also provides a safe hair removal device that does not require any special skills to operate. Because of the complete circuit through coil spring 80, there is minimal risk that electrical current will pass through the skin. Therefore, device 20 will not burn the skin. In addition, because of the rounded shape of both coil spring 80 and the arms 60, 70, there is minimal risk of scraping, scratching, or otherwise harming the skin.

In an alternative embodiment of the present invention, the device is an improved pair of tweezers comprising a first arm and a second arm that are resiliently biased away from two ends of a compressible coil spring. This alternative embodiment does not require use of electrical energy, but is manually operated. To use this embodiment, one or more hairs are placed between the coils of the coil spring. The user then squeezes the first and second arm toward each other, thereby compressing the coil spring which in turn grasps the hair. The user may then pull the hair out from its follicle. Although this device does not provide permanent hair removal, it will provide for a longer lasting hair removal than other methods such as shaving.

Unlike traditional tweezers, this alternative embodiment provides larger opposing surfaces between which hair may be grasped. As a result a user need not be as precise when using this device, and in addition may pull out more than one hair at a time.

The present invention may be embodied in other forms without departing from its spirit or essential characteristics. The described embodiments are to be considered only as illustrative and not as restrictive. The scope of the invention is, therefore, indicated by the appended claims.

What is claimed:

1. A depilatory device comprising:
  a compressible coil spring comprising a plurality of coils for grasping one or more hairs therebetween;
  a first arm and a second arm attached to the coil spring and resiliently biased away from each other such that the coil spring may be compressed by pressing at least one of the first arm and the second arm toward the other arm; and
  electrical means for providing electromagnetic energy to the device to destroy the hair.

2. The depilatory device according to claim 1 further comprising:
  an activating means for activating the electrical means.

3. The depilatory device according to claim 1, wherein the electrical means comprises electrical circuitry.

4. The depilatory device according to claim 3, wherein the electrical means further comprises an AC-DC adapter and a power cord to be plugged into the wall.

5. The depilatory device according to claim 4, further comprising an indicator light for lighting up when the device is plugged in.

6. The depilatory device according to claim 2, wherein the activating means comprises a switch, and wherein the switch is activated by pressing at least one of the first arm and the second arm toward the other arm.

7. The depilatory device according to claim 1, wherein the electrical means provides electromagnetic energy to the coil spring to destroy the hair.

8. The depilatory device according to claim 1, wherein the electromagnetic energy is in the form of radio waves.

9. A depilatory device comprising:
  a compressible coil spring comprising a plurality of coils for grasping one or more hairs therebetween;
  a first arm and a second arm attached to the coil spring and resiliently biased away from each other;
  a first button attached to the first arm;
  a second button attached to the second arm, wherein the coil spring may be compressed by pressing at least one of the first button and the second button, thereby pressing at least one of the first arm and the second arm toward the other arm;
  electrical means for providing radio waves to the coil spring to destroy the hair;
  an activating means for activating the electrical mean; and
  an outer casing enclosing a portion of both first and second arms, wherein the outer casing has a plurality of openings through which the first button, the second button, and the portions of the arms attached to the coil spring extend.

* * * * *